(12) United States Patent
Wang et al.

(10) Patent No.: US 9,348,214 B2
(45) Date of Patent: May 24, 2016

(54) SPECTRAL PURITY FILTER AND LIGHT MONITOR FOR AN EUV RETICLE INSPECTION SYSTEM

(71) Applicant: KLA-Tencor Corporation, Milpitas, CA (US)

(72) Inventors: Daimian Wang, Fremont, CA (US); Li Wang, San Ramon, CA (US); Frank Chilese, San Ramon, CA (US); David Alles, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 143 days.

(21) Appl. No.: 14/170,808

(22) Filed: Feb. 3, 2014

(65) Prior Publication Data

US 2014/0217298 A1 Aug. 7, 2014

Related U.S. Application Data (60) Provisional application No. 61/762,230, filed on Feb. 7, 2013.

(51) Int. Cl.
| | |
|---|---|
| *G01N 21/956* | (2006.01) |
| *G03F 1/00* | (2012.01) |
| *G03F 1/24* | (2012.01) |
| *G03F 1/22* | (2012.01) |
| *G03F 1/84* | (2012.01) |
| *G03F 7/20* | (2006.01) |

(52) U.S. Cl.
CPC ............ *G03F 1/24* (2013.01); *G01N 21/956* (2013.01); *G03F 1/22* (2013.01); *G03F 1/84* (2013.01); *G01N 2021/95676* (2013.01); *G03F 7/70033* (2013.01)

(58) Field of Classification Search
CPC ............... G03F 1/24; G03F 1/22; G03F 1/84; G03F 1/0092; G03F 7/70033; G01N 21/956; G01N 2021/95676
See application file for complete search history.

(56) References Cited

U.S. PATENT DOCUMENTS

| | | |
|---|---|---|
| 6,809,327 B2 | 10/2004 | Bristol |
| 7,084,412 B2 | 8/2006 | Weiss |
| 7,453,645 B2 | 11/2008 | Klunder et al. |

(Continued)

FOREIGN PATENT DOCUMENTS

| | | |
|---|---|---|
| JP | 2006-191090 A | 7/2006 |
| JP | 2007-129209 A | 5/2007 |
| WO | WO 2011000622 A1 * | 1/2011 |

*Primary Examiner* — David Porta
*Assistant Examiner* — Jeremy S Valentiner
(74) *Attorney, Agent, or Firm* — Simpson & Simpson, PLLC (57) ABSTRACT

An extreme ultraviolet (EUM) mask inspection system, comprising a light source to project EUV light along an optical axis, an illumination system to receive the EUV light from the source, the illumination system comprising a spectral purity filter (SPF), the SPF transmits a first portion of the EUV light along the optical axis toward a mask and the SPF comprising a plurality of at least partially reflective elements, said elements reflects a second portion of the EUV light off the optical axis, a projection system adapted to receive the first portion of the EUV light after it has illuminated the mask, a first detector array adapted to receive the image, and a second detector array to receive the second portion of the EUV light. The SPF may comprise one or more multilayer interference-type filters. Alternatively, the SPF comprises a thin film filter disposed on a grazing incidence mirror array.

13 Claims, 5 Drawing Sheets

(56) References Cited

U.S. PATENT DOCUMENTS

| | | |
|---|---|---|
| 8,198,613 B2 | 6/2012 | Moriya et al. |
| 8,536,551 B2 | 9/2013 | Moriya et al. |
| 2006/0221440 A1 | 10/2006 | Banine et al. |
| 2007/0012889 A1* | 1/2007 | Sogard ................ 250/504 R |
| 2010/0043837 A1 | 2/2010 | Grant et al. |
| 2010/0140512 A1* | 6/2010 | Suganuma et al. ........ 250/504 R |
| 2010/0149505 A1* | 6/2010 | Sewell et al. ................ 355/67 |
| 2011/0024651 A1* | 2/2011 | Schimmel et al. ........ 250/504 R |
| 2011/0164237 A1 | 7/2011 | Soer et al. |
| 2011/0223543 A1 | 9/2011 | Banine et al. |
| 2012/0147350 A1 | 6/2012 | Yakunin et al. |
| 2012/0235049 A1 | 9/2012 | Wang |
| 2012/0256105 A1 | 10/2012 | Moriya et al. |

* cited by examiner

PRIOR ART

SPECTRAL PURITY FILTER AND LIGHT MONITOR FOR AN EUV RETICLE INSPECTION SYSTEM

CROSS REFERENCE TO RELATED APPLICATIONS

This patent application claims priority of U.S. Provisional Patent Application No. 61/762,230 filed Feb. 7, 2013, by Wang et al. and titled "EUV Actinic Reticle Inspection System Using Multilayer Beamsplitter for Spectral Purity Filter and Reference Detection." Said application is incorporated herein by reference.

FIELD OF THE INVENTION

The present invention relates to apparatus and methods for reticle inspection providing spectral purification of illumination light and reference detection of the illumination light, and components for use therewith.

BACKGROUND OF THE INVENTION

Lithography systems using deep ultraviolet (UV) illumination at a 193 nm wavelength and corresponding metrology systems are well known, and components for use in such systems have been developed to a significant degree.

A next step in lithography is the use of Extreme Ultraviolet (EUV) illumination in a band about a wavelength of 13.5 nm. Components and corresponding metrology and inspection systems (e.g., actinic reticle inspection systems) for use with EUV light have been developed to a lesser degree.

In one method, to produce EUV light for use in EUV systems, a Nd:YAG laser at a wavelength near 1030 nm operates as a driver laser and projects laser light onto a light source comprising a Xenon target which is stimulated to output the EUV light. In such systems, 1030 nm driver laser light may enter the system or light output from the Xenon target may include light outside of the band desired for illumination of the reticle. Such undesired light transmission may cause thermal damage to a reticle, may cause image flare in a detector image or may have other deleterious effects. Spectral purity filters (SPFs) of various configurations have been proposed to reduce or eliminate unwanted wavelengths of light. U.S. Pat. No. 7,453,645 describes a device including one or more apertures through which light to be filtered is passed. The aperture diameter is selected such that diffraction properties selectively transmit or reflect light of desired wavelengths. United States Patent Publication 2006/0221440 describes a multi-layered, interference, spectral filter in a honeycomb array for use in a lithography system.

Figure 1:
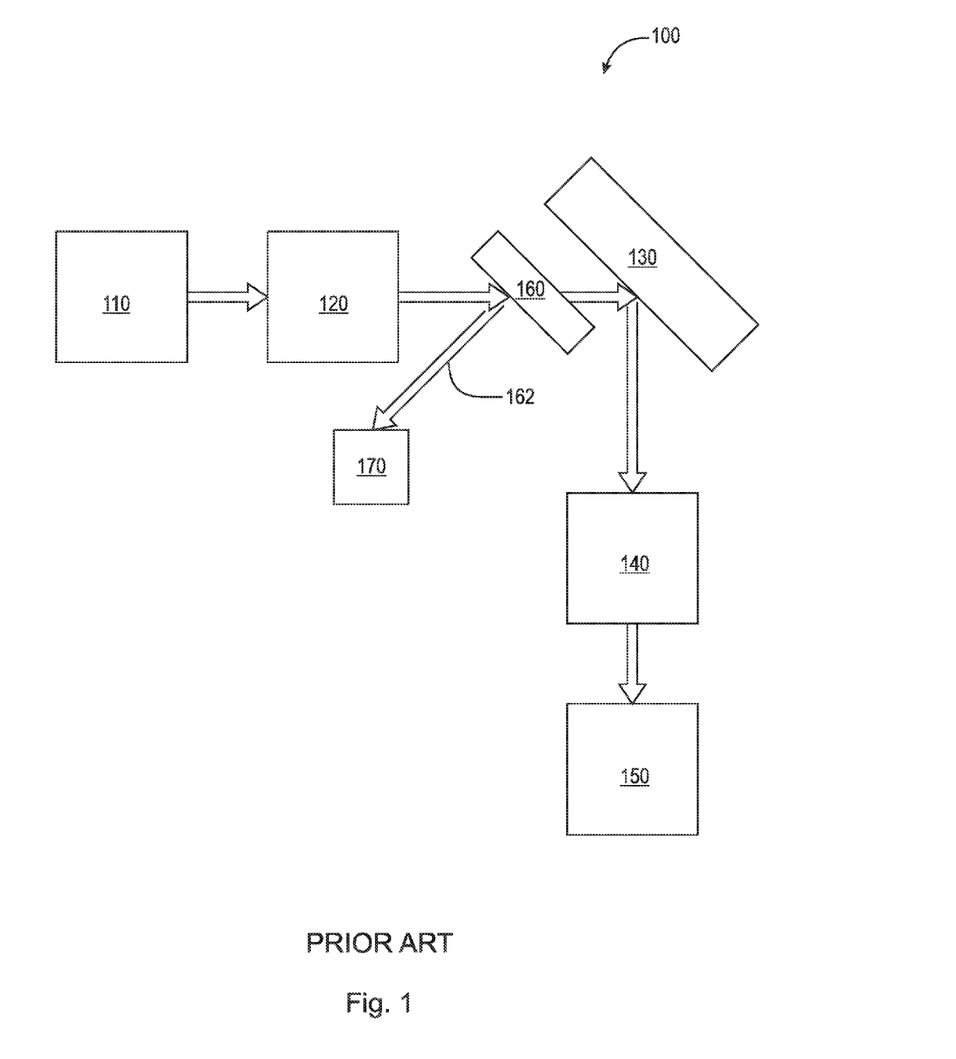
FIG. 1 is a block diagram of a conventional inspection system for use with UV light.

While metrology and inspection systems such as actinic (at-wavelength) reticle inspection systems are known for use with conventional UV systems, such systems are still being developed for use with EUV light. FIG. 1 is a schematic illustration of a conventional inspection system 100 for use with UV light. Inspection system 100 includes a light source 110 to produce the UV light, an illumination system 120 to project light onto reticle 130 (also referred to herein as a mask), a projection system 140 to produce an image of the reticle, and a detector array 150 to receive the image of the reticle for subsequent analysis. Such systems typically include a beam splitter 160 to produce a reference beam 162 to measure stability and uniformity of the UV light beam over time and at different locations within the beam using a light measurement apparatus 170. Such beam splitters are made from conventional beam splitter materials including fused silica, magnesium fluoride or calcium fluoride. Such materials are inappropriate for use with EUV light due to their low transmission rates at EUV wavelengths.

SUMMARY OF THE INVENTION

An aspect of the invention is directed to an extreme ultraviolet (EUV) actinic mask inspection system. The inspection system comprises a light source adapted to project EUV light along an optical axis, an illumination system adapted to receive the EUV light from the light source. The illumination system comprises a spectral purity filter (SPF). The SPF is adapted to transmit a first portion of the EUV light along the optical axis toward a mask and the SPF comprising a plurality of at least partially reflective elements. Said plurality of at least partially reflective elements adapted to reflect a second portion of the EUV light off the optical axis. The inspection system also comprises a projection system adapted to receive the first portion of the EUV light after it has illuminated the mask and thereby form an image of the mask, a first detector array adapted to receive the image of the mask, and a second detector array to receive the second portion of the EUV light. In some embodiments, the plurality of at least partially reflective elements are disposed non-normally to the direction of the optical axis.

The SPF may comprise at least one multilayer interference-type filter having one or more surfaces constituting said plurality of at least partially reflective elements disposed non-normally to the optical axis. Regions of a single multilayer interference-type filter may constitute the plurality of at least partially reflective elements.

In some embodiments, the inspection system comprises a film support structure attached to the filter and disposed between the regions. In some embodiments, the first detector array comprises a plurality of pixels with non-detecting spaces between the plurality of pixels, and wherein the film support structure only images to the non-detecting spaces between the plurality of pixels.

Each multilayer inference-type filter may comprise one or more layers of at least two of Zirconium, Zirconium Silicide, Niobium, Niobium Silicide, Molybdenum, Molybdenum Silicide, Boron and Silicon.

In some embodiments, the first portion of EUV light has a wavelength, and the period of each multilayer filter is equal to about one half of the wavelength.

In some embodiments, the reflectivity of each of the plurality of multilayer filters is at least 1.0% for the EUV light and the transmission of the EUV light is at least 90%. In some embodiments, the SPF comprises a thin film filter disposed on a grazing incidence mirror array. The mirror array may comprise a plurality of mirrors, and each of the plurality of mirrors may comprise a mirror surface disposed at an angle of 3-20 degrees with the direction of the optical axis.

The first detector array may comprise a plurality of pixels with non-detecting spaces between the plurality of pixels, and wherein the SPF comprises a non-optical support structure, wherein the support structure is only imaged to non-detecting spaces between the pixels.

The inspection system may further comprise the mask.

Another aspect of the present invention is directed to a method of inspecting a reticle, comprising projecting EUV light along an optical axis onto a spectral purity filter (SPF) apparatus, the SPF apparatus transmitting a first portion of the EUV light along the optical axis toward a mask and reflecting a second portion of the EUV light off the optical axis; imaging the first portion of the EUV light after it has illuminated the mask; and imaging the second portion of the EUV light to provide an illumination reference.

The step of projecting EUV light may comprise projecting the EUV light onto an SPF that comprises one or more multilayer interference-type filters.

The step of projecting may comprise projecting EUV light onto an SPF comprising a thin film filter disposed on a grazing incidence mirror array.

In some embodiments, each of the one or more multilayer inference-type filter comprises one or more layers of at least two of Zirconium, Zirconium Silicide, Niobium, Niobium Silicide, Molybdenum, Molybdenum Silicide, Boron and Silicon, the first portion of EUV light has a wavelength, and the period of each of the multilayer filters is equal to about one half of the wavelength.

Another aspect of the invention is directed to a spectral purity filter, comprising a plurality of partially reflective elements comprising one or more multilayer interference filters, the plurality of partially reflective elements arranged in a two dimensional array, the elements disposed on axes in a first direction and on axes in a second direction, the first direction and the second direction being perpendicular to one another and, each element having an adjacent element aligned with it along at least one of the first direction or the second direction. The spectral purity filter further comprises a support structure disposed between the elements of the plurality of partially reflective elements.

In some embodiment, each of the one or more multilayer inference-type filters comprises one or more layers of at least two of Zirconium, Zirconium Silicide, Niobium, Niobium Silicide, Molybdenum, Molybdenum Silicide, Boron and Silicon. The period of each of the multilayer filters may be equal to about one half of a wavelength of EUV light.

In some embodiments, the reflectivity of the multilayer filter is at least 1.0% for the EUV light and the transmission of the EUV light is at least 90%.

Another aspect of the invention is directed to a spectral purity filter, characterized by a first axis, a second axis and a third axis that are mutually perpendicular to one another, the filter comprising: a two dimensional array of channels disposed in a plane defined by the first axis and the second axis, each channel defined in the direction of the first axis by an upper side and a lower side, and defined in the direction of the second axis by, a right side, a left side. Each channel extends along the third axis. A same one of said upper side, a right side, a left side and a lower side, for each channel, has a mirror surface attached thereto. Each mirror surface is disposed at an angle relative to said one of said upper side, lower side, right side and left side, in the direction of the third axis, such that the mirror surfaces at least partially face a proximal end of the SPF along the third axis of the spectral purity filter. The spectral purity filter further comprises a thin film filter disposed to cover each channel at the proximal end of the spectral purity filter.

Each mirror surface may be disposed at an angle of 3-20 degrees with the direction of the third axis. In some embodiments, each mirror surface comprises Ruthenium.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Same reference numerals refer to the same elements throughout the various figures. Furthermore, only reference numerals necessary for the description of the respective figure are shown in the figures. The shown embodiments represent only examples of how the invention can be carried out. This should not be regarded as limiting the invention.

Figure 2:
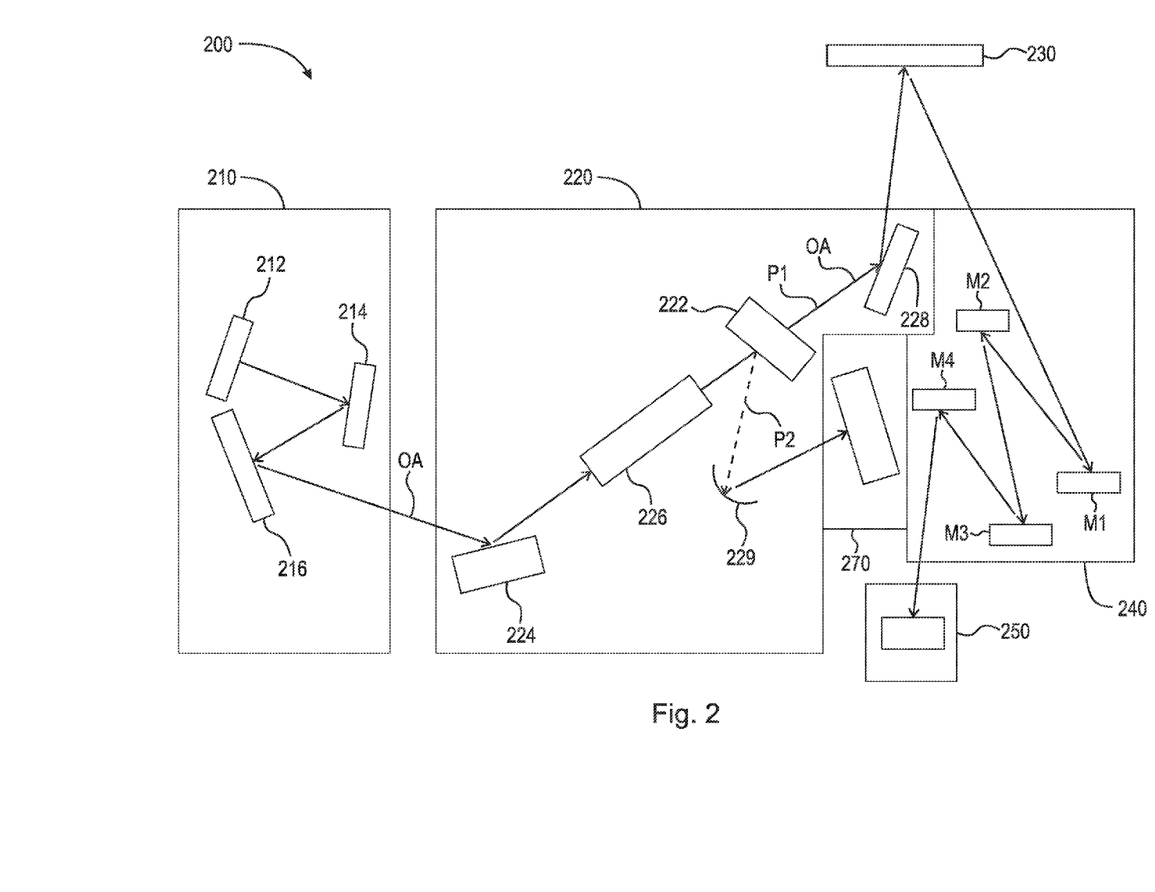
FIG. 2 is a schematic diagram of an example of an inspection system providing spectral purification and reference detection of EUV light according to aspects of the present invention.

FIG. 2 is a schematic diagram of an example of an extreme ultraviolet (EUV) actinic mask inspection system 200 providing spectral purification and reference detection according to aspects of the present invention. Inspection system 200 comprises a light source 210, an illumination system 220 providing spectral purification and facilitating reference detection, a projection system 240, a first detector array 250, and a second detector array 270 for inspecting a mask 230.

Light source 210 is adapted to produce EUV light in a conventional manner and projects the light along an optical axis OA. Light source 210 may have any suitable configuration to produce light having a desired wavelength or band of wavelengths. For example, as shown in the illustrated embodiment, a Nd:YAG laser 212 producing light at 1030 nm is projected onto a Xenon fuel source 214 to produce EUV light. A collector 216 receives the EUV light from fuel source 210 and directs the light along the optical axis OA.

Illumination system 220 is adapted to receive the EUV light from the light source 210 and comprises a spectral purity filter (SPF) 222. In the illustrated embodiment, in addition to spectral filtering, the illumination system processes and shapes the light prior to projection onto the mask using a relay 224, a homogenizer 226, and a condenser 228. Any suitable beam shaping apparatus may be used to appropriately illuminate mask 230.

According to aspects of the present invention, SPF 222 is adapted to transmit a first portion P1 of the EUV light along the optical axis OA onto mask 230, and SPF 222 comprises a plurality of at least partially reflective elements disposed non-normally to optical axis OA such that said plurality of surfaces is adapted to reflect a second portion P2 of the EUV light off-axis. In the illustrated embodiment, the SPF is located proximate the exit of homogenizer 226 and configured and arranged to direct second portion of light P2 to second detector array 270 such that an image of the light profile at the homogenizer exit is formed at the second detector array 270 by one or more optics 229. Further details of embodiments of SPF are given below with reference to FIGS. 3A-4B.

Second detector array 270 is disposed in a location to receive the second portion P2 of the EUV light. The second portion of the EUV light constitutes a reference portion of the EUV light for reference detection. The second detector array operates as a reference detector and the output of the second detector array may be processed in a conventional manner to indicate any spatial variations and temporal variations that may exist in the first portion of light that is used to illuminate the mask.

Projection system 240 is adapted to receive the first portion P1 of the EUV light after it has illuminated mask 230 and to form an image of mask 230. Projection system 240 constitutes a conventional image forming system comprising one or more optical elements such as mirror M1, M2, M3 and M4.

First detector array 250 is adapted to receive the image of mask 230 from projection system 240. For example, the first detector array 250 is a conventional Time Delay Integration (TDI) device for receiving the image of mask 230, and may alternately be a CCD or a diode array of suitable configuration to receive the light from the mask.

Figure 3A:
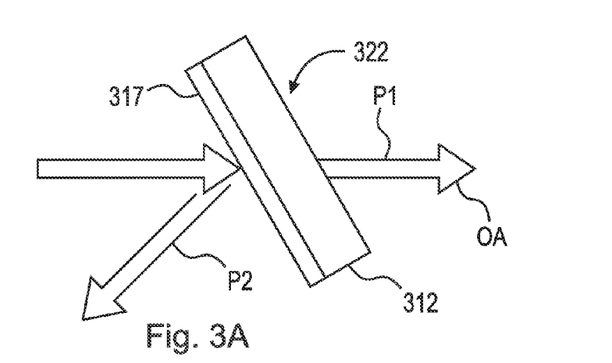
FIG. 3A is a schematic illustration of an example of an embodiment of a spectral purification filter (SPF) disposed to receive the output of a EUV source according to aspects of the present invention.
Figure 3B:
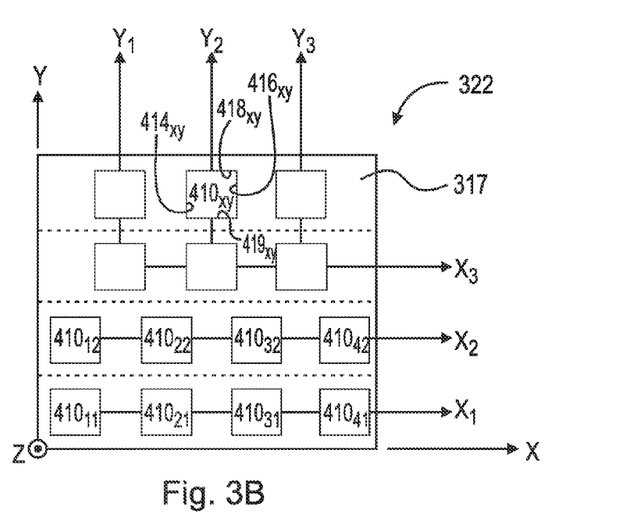
FIG. 3B is a plan view of the SPF of FIG. 3A.
Figure 3C:
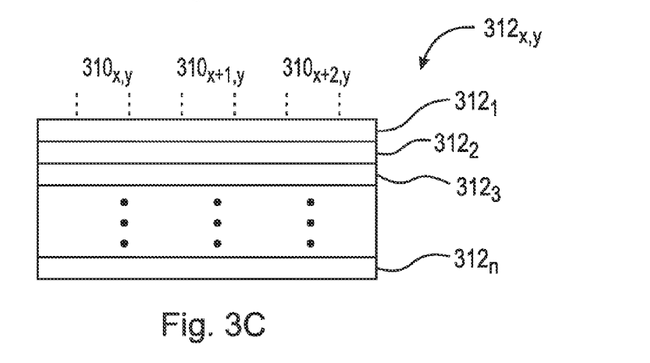
FIG. 3C is a cross-sectional view of a multilayer, interference-type filter of the SPF of FIG. 3B.

An example of an embodiment of a spectral purification filter 322 that is comprised of at least one multilayer interference-type filters according to aspects of the present invention will be described with reference to FIGS. 3A-3C. Spectral purification filter 322 is disposed to receive the output of the EUV source. FIG. 3A is a schematic illustration of spectral purification filter 322. FIG. 3B is a plan view of SPF 322. FIG. 3C is a cross-sectional view of a multilayer interference-type filter of SPF 328.

SPF 322 is adapted to transmit a first portion P1 of the EUV light along the optical axis OA onto a mask 230 (shown in FIG. 2), and the SPF comprises a plurality of at least partially reflective elements $310_{xy}$ disposed non-normally to the optical axis OA such that each of said plurality of elements is adapted to reflect a second portion P2 of the EUV light away from optical axis OA. In the illustrated embodiment, partially reflective elements $310_{xy}$ correspond to regions of a single multilayer interference-type filter that is big enough to cover the entire area of SPF 322 in the x-y dimensions. FIG. 3C shows the regions corresponding to elements $310_{xy}$ on filter 312.

In the illustrated embodiment, SPF 322 comprises a single multilayer interference-type filter 312, wherein different regions of the multilayer filter constitute the plurality of the at least partially reflective elements disposed non-normally to the optical axis OA. Alternatively, a plurality of multilayer interference-type filters 312 may be used, with each multilayer filter or portions thereof corresponding to one or more of the at least partially reflective elements $310_{xy}$. In such an embodiment, the plurality of multilayer filters or portions thereof constitute the plurality of at least partially reflective elements disposed non-normally to the optical axis OA.

In the illustrated embodiment, multilayer interference-type filter 320 is disposed on a film support structure 317. The support structure increases the mechanical robustness of SPF 322 and increases the heat dissipation abilities of SPF 322. The layout of the elements $310_{xy}$ and the film support structure 317 are selected such that the light from elements $310_{xy}$ image onto the detector pixels of the first detector array 250 (after said light illuminates mask 230) and onto the detector pixels of the second detector array 270; the film support structure images to non-detecting spaces between the detector pixels of the first detector array 250. In some embodiments, the film support structure only images to non-detecting spaces between the detector pixels of the first detector array 250.

As shown in FIG. 3B, in the illustrated embodiment, the at least partially reflective elements $310_{xy}$ are arranged in a two-dimensional array. The elements are disposed on axes $x_1$, $x_2$, $x_3$ ... $x_n$ in a first direction x, and on axes $y_1$, $y_2$, $y_3$ ... $y_n$ in a second direction y. The first direction and the second direction are perpendicular to one another. It will also be appreciated that each element $310_{xy}$ has an adjacent element $310_{xy}$ aligned with it along the first direction x and/or the second direction y (i.e., the centers of the adjacent elements are aligned along first direction x and/or the second direction y). A support structure 317 is disposed between the filters $310_{xy}$ of the plurality of multilayer interference filters.

The layers $312_{xy}$ of the multilayer structure are selected such that elements $310_{xy}$ block light (e.g., 1030 nm light) from the drive laser 212 (shown above in FIG. 2) from reaching mask 230. For example, the multilayer structure may comprise alternating layers of Zirconium, Zirconium Silicide, Niobium, Niobium Silicide, Molybdenum, Molybdenum Silicide, Boron and Silicon. Typically, in a given multilayer structure, alternating layers of only two of said material will be used.

An acceptable structure should have suitable mechanical strength characteristics. For example, to achieve a suitable strength, the overall thickness of the multilayer structure may be greater than 18 nm, and in some embodiments, at least 20 nm. An acceptable structure should also have suitable reflectivity to provide a signal strength with a suitable signal-to-noise ratio at second detector array 270 (shown in FIG. 2). For example, the reflectivity should be at least 0.5 percent for EUV light, in some embodiments, at least 1.0%, and in some embodiments at least 5%. Also, an acceptable structure should also have a suitable transmission efficiency for EUV light. For example, the transmission should be at least 70%, in some embodiments at least 80%, and in some embodiments at least 90%. In some embodiments, an acceptable structure reduces the intensity of any laser light by a factor of 100, and reduce the intensity of any non-EUV UV light by a factor of 10.

It is to be appreciated that, to achieve suitable performance, the structure chosen by the inventors has a period (i.e., two layers of material) equal to about one-half of the wavelength of the EUV light being used for illumination of mask 230. In some some embodiments, the periods are within +/−20% of the wavelength; in other embodiments the periods are within +/−10% of the wavelength; and in other embodiments, the periods are within +/−5% of the wavelength. While such a configuration is usually associated with a high reflectivity, the number of layers in the multilayer stack is relatively low thereby reducing the efficiency of the reflectivity achieved by the stack and increasing transmission efficiency of EUV light.

In one embodiment of a suitable structure for use with EUV light at 13.5 nm, the period of the Zirconium/Silicon structure is about 7 nm (i.e., the Zirconium and Silicon layers are each chosen to be 3.5 nm) and 6 periods are used (i.e., six total layers of Zirconium and six total layers of Silicon). The calculated, theoretical reflectivity is about 5% and the calculated, theoretical EUV absorption loss is about 5%, resulting in a 90% transmission of EUV light. In addition to the multilayer structure, a coating of Ruthenium or other EUV transmitting, non-oxidizing material may be added to the surface of the structure to prevent oxidation.

Figure 4A:
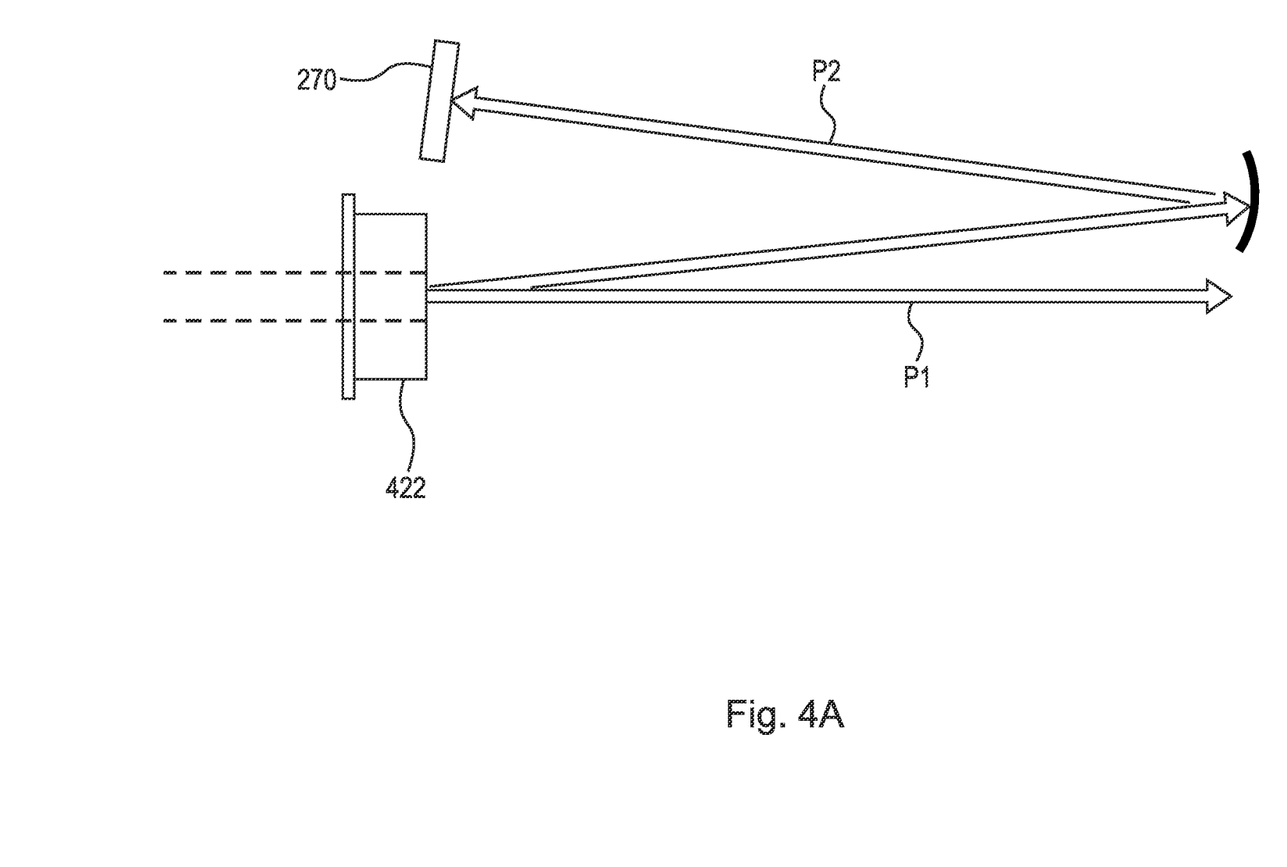
FIG. 4A is a schematic illustration of another example of an embodiment of a spectral purification filter disposed to receive the output of the EUV source according to aspects of the present invention.

FIG. 4A is a schematic illustration of an example of an embodiment of a spectral purification filter that is disposed to receive and split the output of the EUV source 210 (shown in FIG. 2) according to aspects of the present invention. The SPF is adapted to transmit a first portion P1 of the EUV light along optical axis OA onto a mask 230 (shown in FIG. 2), and the SPF comprises a plurality of at least partially reflective elements $412_{xy}$ (shown in FIG. 4B) disposed non-normally to optical axis OA such that each of said plurality of surfaces $412_{xy}$ is adapted to reflect a second portion P2 of the EUV light off-axis.

Figure 4B:
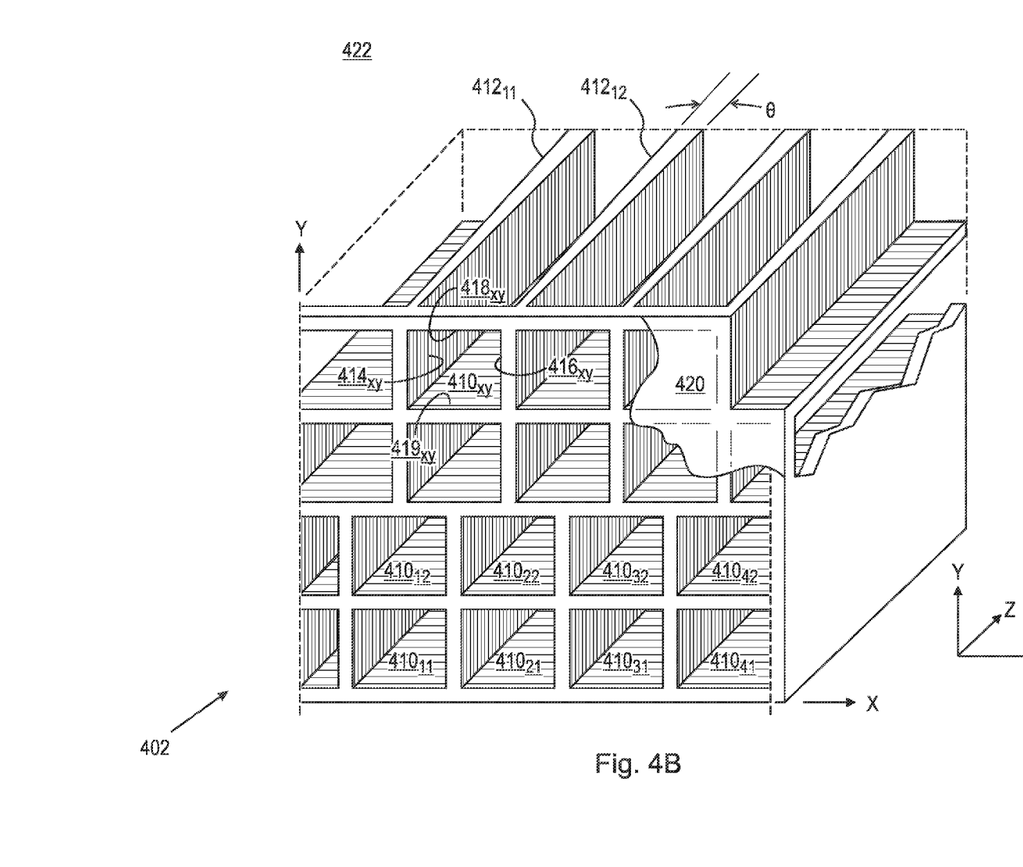
FIG. 4B is a projection view of the SPF of FIG. 4A.

FIG. 4B is a perspective view of the SPF 422. SPF 422 comprises a thin film filter 420 disposed on a grazing incidence mirror array 412. The thin film filter 420 can be made using single or multiple layers of materials that have relatively high EUV transmission and low non-EUV band transmission. The materials can be, for example, Zirconium, Zirconium Silicide, Niobium, Niobium Silicide, Molybdenum, Molybdenum Silicide, Boron and Silicon. In this embodiment, if a multilayer structure is chosen, layer thicknesses are chosen to achieve appropriate transmission, and the layer thicknesses relative to the EUV wavelength are not chosen to achieve a particular reflectivity because the film is not used to reflect light for reference detection. Mirror array 412 reflects light into portion P2.

SPF 400 is characterized by a first axis x, a second axis y and a third axis z that are mutually perpendicular to one another. The filter comprises a two-dimensional array of channels $410_{xy}$ disposed in a plane defined by the first axis x and the second axis y. Each channel is defined in the direction of the first axis x by a left side $414_{xy}$ and a right side $416_{xy}$, and is defined in the direction of the second axis y by, an upper side $418_{xy}$, and a lower side $419_{xy}$. Each channel extends along the third axis z. A same one of said upper side, right side, left side and lower side, for each channel, has a mirror surface $412_{xy}$ extending over said side and attached thereto. For each channel, the mirror surface is disposed at an angle θ relative to said one of said upper side, lower side, right side and left side, in the direction of the third axis z, such that the mirror surface at least partially faces a proximal end 402 of the SPF along the third axis z of the spectral purity filter. A spectral filter 420 is disposed to cover each channel $410_{xy}$ at the proximal end 402 of the spectral purity filter.

For example, the grazing incidence mirror array 412 of SPF 400 can be formed by etching a small silicon cube (e.g., 2 mm×2 mm×2 mm) using anisotropic etching of the silicon crystals 111 plane. For example, the mirror surfaces $412_{xy}$ can be coated with stainless steel or ruthenium to achieve high reflectivity. For example, mirror surfaces $412_{xy}$ may be disposed at an angle θ equal to 3-20 degrees relative to the Z-axis direction. It will be appreciated that in the illustrated embodiment the Z-axis is aligned with the optical axis OA. Regions between the channels may include non-optical support regions, which may be non-transparent and direct light neither into first portion P1 nor second portion P2.

It will be appreciated that light incident on a mirror surfaces $412_{xy}$ will be deflected off-axis to the first detector array (shown above in FIG. 2) and light passing through the SPF channels without reflection from mirror array will illuminate mask 230 (shown in FIG. 2). It will be appreciated that the length of channels $410_{xy}$ in the z-direction determines in-part the relative strengths of portion P1 and portion P2, and the length is selected to achieve suitable portion strengths.

As described above with reference to elements $310_{xy}$ of SPF 322, the locations of the channels $410_{xy}$ and mirrors $412_{xy}$ are selected such that the light from channels $410_{xy}$ that is transmitted in portion P1 images onto the detector pixels of the first detector array 250 as shown in FIG. 2 (after said light illuminates mask 230) and the light reflected into portion P2 images onto the detector pixels of the second detector array 270. In some embodiments, any support structure between the channels images to non-detecting spaces between the detector pixels of the first detector array 250. It will be appreciated that it is typically desirable that the film support structure only images to non-detecting spaces between the detector pixels of the first detector array 250.

The invention has been described with reference to specific embodiments. It is obvious to a person skilled in the art, however, alterations and modifications can be made without leaving the scope of the subsequent claims.

What is claimed is:

1. An extreme ultraviolet (EUV) mask inspection system, comprising:
    a light source adapted to generate EUV light along an optical axis;
    an illumination system adapted to receive the EUV light from the light source, the illumination system comprising a spectral purity filter (SPF), the SPF adapted to transmit a first portion of the EUV light along the optical axis toward a location for a mask, the spectral purity filter characterized by a first axis and a second axis, the first axis, second axis and optical axis being mutually perpendicular to one another, the filter comprising
        (i.) a two dimensional array of channels disposed in a plane defined by the first axis and the second axis, each channel defined in the direction of the first axis by an upper side and a lower side, and defined in the direction of the second axis by, a right side, a left side, each channel extending in the direction of the optical axis and
        (ii.) a same one of said upper side, right side, left side and lower side, for each channel, having a mirror surface attached thereto, and each mirror surface disposed at an angle relative to said one of said upper side, lower side, right side and left side, each of the mirror surfaces at least partially facing in a direction parallel to the optical axis toward a proximal end of the SPF; and
        (iii.) the channels covered by a thin film filter;
    a projection system adapted to receive the first portion of the EUV light after it has illuminated the location and thereby form an image of the mask;
    a first detector array adapted to receive the image of the mask; and
    a second detector array to receive the second portion of the EUV light.

2. The inspection system of claim 1, wherein the mirror surfaces are disposed non-normally to the direction of the optical axis.

3. The inspection system of claim 1, wherein the thin film filter comprises one or more layers of at least two of Zirconium, Zirconium Silicide, Niobium, Niobium Silicide, Molybdenum, Molybdenum Silicide, Boron and Silicon.

4. The inspection system of claim 1, wherein the mirror surfaces constitute a grazing incidence mirror array.

5. The inspection system of claim 4, wherein the mirror array comprises a plurality of mirrors, and
    wherein each of the plurality of mirrors comprises a mirror surface disposed at an angle of 3-20 degrees with the direction of the optical axis.

6. The inspection system of claim 4, wherein the first detector array comprises a plurality of pixels with non-detecting spaces between the plurality of pixels, and wherein the SPF comprises a non-optical support structure, wherein the support structure is only imaged to non-detecting spaces between the pixels.

7. The inspection system of claim 1, further comprising the mask.

8. A method of inspecting a reticle, comprising:
   projecting EUV light along an optical axis onto a spectral purity filter (SPF), the spectral purity filter, characterized by a first axis and a second axis, the first axis, second axis and optical axis being mutually perpendicular to one another, the filter comprising
   (i.) a two dimensional array of channels disposed in a plane defined by the first axis and the second axis, each channel defined in the direction of the first axis by an upper side and a lower side, and defined in the direction of the second axis by, a right side, a left side, each channel extending along the optical axis and
   (ii.) a same one of said upper side, right side, left side and lower side, for each channel, having a mirror surface attached thereto, and each mirror surface disposed at an angle relative to said one of said upper side, lower side, right side and left side, each of the mirror surfaces at least partially facing in a direction parallel to the optical axis toward a proximal end of the SPF; and
   (iii) the channels covered by a thin film filter;
   the SPF apparatus transmitting a first portion of the EUV light along the optical axis toward a mask;
   specularly reflecting a second portion of the EUV light off the optical axis using the mirrors;
   imaging the first portion of the EUV light after it has illuminated the mask; and
   imaging the second portion of the EUV light to provide an illumination reference.

9. The method of claim 8, wherein the mirrors constitute a grazing incidence mirror array.

10. The method of claim 8, wherein the thin film filter comprises one or more layers of at least two of Zirconium, Zirconium Silicide, Niobium Silicide, Molybdenum, Molybdenum Silicide, Boron and Silicon.

11. A spectral purity filter, characterized by a first axis, a second axis and a third axis that are mutually perpendicular to one another, the filter comprising:
    a two dimensional array of channels disposed in a plane defined by the first axis and the second axis, each channel defined in the direction of the first axis by an upper side and a lower side, and defined in the direction of the second axis by, a right side, a left side, each channel extending along the third axis and
    a same one of said upper side, right side, left side and lower side, for each channel, having a mirror surface attached thereto, and each mirror surface disposed at an angle relative to said one of said upper side, lower side, right side and left side, each of the mirror surfaces at least partially facing in a direction parallel to the third axis of the spectral purity filter toward the proximal end of the SPF; and
    a thin film filter disposed to cover each channel.

12. The filter of claim 11, wherein each mirror surface is disposed at an angle of 3-20 degrees with the direction of the third axis.

13. The filter of claim 11, wherein each mirror surface comprises Ruthenium.

\* \* \* \* \*